United States Patent [19]

Shih et al.

[11] Patent Number: 5,712,147
[45] Date of Patent: Jan. 27, 1998

[54] DNA ENCODING *BACILLUS LICHENIFORMIS* PWD-1 KERATINASE

[75] Inventors: Jason C. H. Shih, Cary; Xiang Lin; Eric S. Miller, both of Raleigh, all of N.C.

[73] Assignee: North Carolina State University, Raleigh, N.C.

[21] Appl. No.: 685,774

[22] Filed: Jul. 24, 1996

Related U.S. Application Data

[63] Continuation of Ser. No. 250,028, May 27, 1994, abandoned.

[51] Int. Cl.$^6$ .............................. C12N 9/56; C12N 1/20; C12N 15/00; C07H 21/04
[52] U.S. Cl. ............... 435/222; 435/252.33; 435/252.5; 435/320.1; 536/23.2
[58] Field of Search .................................. 435/219, 222, 435/252.33, 252.5, 320.1; 536/23.2

[56] References Cited

U.S. PATENT DOCUMENTS

| | | | |
|---|---|---|---|
| 4,908,220 | 3/1990 | Shih et al. | 426/61 |
| 4,959,311 | 9/1990 | Shih et al. | 435/681.1 |
| 5,063,161 | 11/1991 | Shih et al. | 435/252.5 |
| 5,171,682 | 12/1992 | Shih et al. | 435/222 |
| 5,186,961 | 2/1993 | Shih et al. | 426/2 |

FOREIGN PATENT DOCUMENTS 0 348 814    1/1990    European Pat. Off. .

OTHER PUBLICATIONS

Jacobs et al. (1985) Nucleic Acids Research 13(24); 8913–8926.

*Primary Examiner*—Charles L. Patterson, Jr.
*Assistant Examiner*—Lisa J. Hobbs
*Attorney, Agent, or Firm*—Myers Bigel Sibley & Sajovec, LLP

[57] ABSTRACT

An isolated DNA encoding a keratinase is disclosed. The isolated DNA may be any of (a) isolated DNA which encodes the *Bacillus licheniformis* PWD-1 keratinase enzyme of FIG. 1, (b) isolated DNA which hybridizes to an oligonucleotide probe, which hybridizes to the DNA of (a) above, and does not hybridize to DNA encoding the *Bacillus licheniformis* NCIB 6816 subtilisin Carlsberg serine protease, and (c) isolated DNA differing from the isolated DNAs of (a) and (b) above in nucleotide sequence due to the degeneracy of the genetic code, and which encodes a keratinase enzyme.

4 Claims, 2 Drawing Sheets

```
PWD-1  CTCCTGCCAAGCTGAAGCGGTCTATTCATACTTTCGAACTGAACATTTTTCTAAAACAGTTNNTAATAACCAAAAAATTTAAATTGGCC   90
Carlsberg  CTCCAAAAAAATAGGCCTACCATATAATTCATTTTTTTTCTATAATAATTAACAGAATAATTGGAATAGATTATATTATCCTTCTATTT  180
                                                        ↑ Preproprotein
                            M  M  R  K  K  S  F  W  L  G  M  L  T  A  F  M  L  V  F
       AAATTATTCTGAATAAAGAGGAGAGTGAGTAATGATGAGGAAAAGAGTTTTTGGCTTGGGATGCTGACGGCCTTCATGCTCGTGTT  270
                                   ↑ Proprotein
       T  M  A  F  S  D  S  A  S  A  A  Q  P  A  K  N  V  E  K  D  Y  I  V  G  F  K  S  G  V  K
       CACGATGGCATTCAGCGATTCCGCTCTGCTGCTCAACCGGCGAAAAATGTTGAAAAGGATTATATTGTCGGATTTAAGTCAGGAGTGAA  360
                    128
       T  A  S  V  K  K  D  V  I  K  E  S  G  G  K  V  D  K  Q  F  R  I  I  N  A  A  K  A  K  L
                         a
       AACCGCATCTGTCAAAAAGGACGTCATCAAAGAGAGTGGGGGCAAAGTGGACAAGCAGTTTAGAATCATCAACGCAGCAAAAGCGAAGCT  450
                                                               ↑ Matura
       D  K  E  A  L  K  E  V  K  N  D  P  D  V  A  Y  V  E  E  D  H  V  A  H  A  L  A  Q  T  V
                                                                     g
       AGACAAAGAGGCGCTTAAGGAAGTCAAAAATGATCCGGATGTCGCTTATGTGGAAGAGGATCATGTGGCCCATGCTTGGGCAAACCGT  540
       P  Y  G  I  P  L  I  K  A  D  K  V  Q  A  Q  G  F  K  G  A  N  V  K  V  A  V  L  D  T  G
       TCCTTACGGCATTCCTCTCATTAAAGCGGACAAAGTGCAGGCTCAAGGCTTCAAGGGAGCGAATGTAAAAGTAGCCGTCTTGGATACAGG  630
       I  Q  A  S  H  P  D  L  N  V  G  G  A  S  F  V  A  G  E  A  Y  N  T  D  G  N  H  G
       AATCCAAGCTTCTCATCCGGACTTGAACGTAGTAGGCGGAGCAAGCTTTGTGGCTGGCGAAGCTTATAACACCGACGGCAACGGACACGG  720
       T  H  V  A  G  T  V  A  A  L  D  N  T  G  V  L  G  V  E  P  S  V  S  L  Y  A  V  K  V
       CACACATGTTGCCGGTACAGTAGCTGCGCTTGACAATACAGGGGTTGTATTAGGCGTTGAGCCAAGCGTATCCTTGTACGCGGTTAAAGT  810
```

FIG. 1A.

```
              L  N  S  S  G  S  G  S  Y  S   G  I  V  S  G  I  E  W  A  T   T  N  G  M  D  V  I  N  M  S
             ACTGAATTCAAGCGGAAGCGGATCATACAGCGGCATTGTAAGCGGAGTCGAGTGGGGCGACAAACGGGACAGTGGATGTTATCAATATGAGT    900
                              a  t                                                            c  .g
              P128
              L  G  A  S  G  S  T  A  M  K   Q  A  V  D  N  A  Y  A  R  G   V  V  V  A  A  G  N
             CCTTGGGGGGAGCATCAGGCTCGACAGCAGTGAAACAGGCGGATGAACGGCATATGCAAGAGGGGTTGTCGTTGTAGCTGCAGCAGGGAA        990
             t     a .c                                             g                    g .g. t
              S  G  S  S  G  N  T  N  T  I   G  Y  P  A  K  Y  D  S  V  I   A  V  G  A  V  D  S  N  S  N
             CAGCGGGATCTTCAGGAGGAAACACGAATACAATTGGCTATCCTGCGAAATACGATTCTGTCATCGCTGTTGGTGCGGTAGACTCTAACAGCAA     1080
                              .c                                               a  .c                t
                                                                              S211
              R  A  S  F  S  S  V  G  A  E   L  E  V  M  A  P  G  A  G  V   Y  S  T  Y  P  T  N  T  Y  A
             CAGAGCTTCATTTCCAGTGTGGGAGCAGAGCTTGAAGTCATGGCTCCTGGCGCAGGGGTATACAGCACTTACCCAACGAACACTTATGC         1170
                         .c  c                                                    .g             c  g
              T  L  N  G  T  S  M  V  S  P   H  V  A  G  A  A  L  I  L  S   K  H  P  N  L  S  A  S  Q
             AACATTGAACGGAACGTCAATGGTTTCTCCTCATGTAGCGGGAGCAGCTTTGATCTTGTCAAAACATCCGAACCTTTCAGCTTCACA           1260
                                                                                                a  t
              V  R  N  R  L  S  S  T  A  T   Y  L  G  S  S  F  Y  Y  G  K   G  L  I  N  V  E  A  A  A  Q
             AGTCCGCAACCGTCTCCTCCAGCACGGGACTTATTTGGGAGCTCCTTCTACTATGGGAAAGGTCTGATCAATGTCGAAGCTGCCGCTCA         1350
                                                                  .t                                  ac  .t
              stop
             ATAACATATTCTAACAAATAGCATATATGAAAAAAGCTAGTGTTTTTAGCACTAGCTTTTTCTTCATTCTGATGAAGGTTGTCCAATATTTT        1440
                                              a                                        g
             GAATCCGTTCCATGATC   1457
                   .      g
```

FIG. 1B.

DNA ENCODING *BACILLUS LICHENIFORMIS* PWD-1 KERATINASE

This is a continuation of application Ser. No. 08/250,028 filed on May 27, 1994, now abandoned.

This invention was made with Government support under a grant from the USDA. The Government has certain rights to this invention.

FIELD OF THE INVENTION

The present invention relates to DNA encoding the *Bacillus licheniformis* PWD-1 keratinase, which is useful for producing a keratinase that is useful for degrading keratins such as feather and producing amino acids therefrom.

BACKGROUND OF THE INVENTION

Feathers are produced in large quantities by the poultry industry. These feathers provide an inexpensive source of raw material for a variety of potential uses. Among other things, there has been considerable interest in developing methods of degrading feathers so they can be used as an inexpensive source of amino acids and digestible protein in animal feed. Processes for converting feather into animal feed which have been developed to date include both steam hydrolysis processes and combined steam hydrolysis and enzymatic processes. See, e.g., Papadopoulos, M. C., *Animal Feed Science and Technology* 16:151 (1986); Papadopoulos, M. C., *Poultry Science* 64:1729 (1985); Alderibigde, A. O. et al., *J. Animal Science* 1198 (1983); Thomas and Beeson, *J. Animal Science* 45:819 (1977); Morris et al., *Poultry Science* 52:858 (1973); Moran et al., *Poultry Science* 46:456 (1967); Davis et al., Processing of poultry by-products and their utilization in feeds, Part I, USDA Util. Res. Rep. no. 3, Washington, D.C. (1961). Disadvantages of these procedures, such as the degradation of heat sensitive amino acids by steam processes and the relatively low digestibility of the resulting products, have lead to continued interest in economical new feather degradation procedures which do not require a harsh steam treatment. Accordingly, an object of the present invention is to provide a process for hydrolyzing keratinaceous material which does not depend upon steam hydrolysis.

An additional object is to provide a process for converting keratinaceous material into amino acids at high yields of the amino acids.

A further object of this invention is to provide a hydrolyzed feather product useful as a feed ingredient which is highly digestible and provides a good quality source of dietary protein and amino acids.

A further object of this invention is to provide a keratinase enzyme which can be utilized as a feed additive to improve the digestibility of keratin and other proteins in feeds.

A still further object of the present invention is to provide an economical animal feed which employs a hydrolyzed feather product as a dietary amino acid source. The foregoing and other objects and aspects of the present invention are explained in detail in the Summary, Detailed Description, and Examples which follow.

SUMMARY OF THE INVENTION

A first aspect of the present invention is isolated DNA encoding a keratinase selected from the group consisting of:

(a) isolated DNA which encodes the *Bacillus licheniformis* PWD-1 (ATCC Accession No. 53757) Keratinase of FIG. 1 (SEQ ID NO: 1);

(b) isolated DNA which hybridizes to isolated DNA of (a) above under conditions represented by a wash stringency of 0.3M NaCl, 0.03M sodium citrate, and 0.1% SDS at 60° C., which is at least 65% homologous to the isolated DNA of (a) above, and which encodes a keratinase enzyme;

(c) isolated DNA which hybridizes to an oligonucleotide probe, which oligonucleotide probe hybridizes to DNA of (a) above, and which oligonucleotide probe does not hybridize to DNA encoding the *Bacillus licheniformis* NCIB 6816 subtilisin Carlsberg serine protease (of which the *B. licheniformis* PWD-1 keratinase appears to be a variant) under the same hybridization conditions; and (d) isolated DNA differing from the isolated DNAs of (a) and (b) above in nucleotide sequence due to the degeneracy of the genetic code, and which encodes a keratinase enzyme.

A second aspect of the present invention is a recombinant DNA molecule comprising vector DNA and a DNA as given above which encodes a keratinase enzyme.

A third aspect of the present invention is a host cell containing a recombinant DNA sequence as given above and capable of expressing the encoded keratinase enzyme.

A fourth aspect of the present invention is a method of making a keratinase enzyme by culturing a host cell as described above under conditions that permit expression of the encoded keratinase, and collecting the expressed keratinase.

The foregoing and other aspects of the present invention are explained in detail in the drawings, Examples, and Detailed Description set forth below.

BRIEF DESCRIPTION OF THE DRAWINGS

FIG. 1 illustrates the sequence and the encoded amino acids of an isolated DNA encoding the *Bacillus licheniformis* PWD-1 keratinase. In addition, FIG. 1 illustrates the variances between the amino acids encoding the *Bacillus licheniformis* PWD-1 keratinase and *Bacillus licheniformis* NCIB 6816 subtilisin Carlsberg gene.

DETAILED DESCRIPTION OF THE INVENTION

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (November 1990) (U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference).

A. DNAs Encoding Keratinase Enzyme

DNAs which encode a keratinase enzyme degrade a keratin source such as feathers. This definition is intended to encompass natural allelic variations in the DNAs. Hybridization conditions which will permit other DNA sequences which code on expression for a keratinase to hybridize to a DNA sequence as given herein are, in general, high stringency conditions. For example, hybridization of such sequences may be carried out under conditions represented by a wash stringency of 0.3M NaCl, 0.03M sodium citrate, 0.1% SDS at 60° C. or even 70° C. to DNA disclosed herein in a standard in situ hybridization assay. See J. Sambrook et al., Molecular Cloning, A Laboratory Manual (2d Ed. 1989) (Cold Spring Harbor Laboratory)). In general, DNA sequences which code for a keratinase and hybridize to the DNA sequence encoding the *Bacillus licheniformis* PWD-1 keratinase disclosed herein will be at least 65%, 70%, 75%, 80%, 85%, 90%, or even 95% homologous or more with the sequence of the keratinase disclosed herein.

Further, DNA sequences (or oligonucleotides) which code for the same keratinase as coded for by the foregoing sequences, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

DNA sequences (or oligonucleotides) which code for the same keratinase as coded for by the foregoing sequences, but which differ in codon sequence from these due to site directed mutigenesis are yet another aspect of this invention. Site directed mutagenesis techniques useful for improving the properties of the keratinase enzyme are well known, as described below. See e.g., U.S. Pat. No. 4,873,192 to Kunkel.

B. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

The DNA encoding keratinase may be made according to any of the known techniques. For example, the DNA may be constructed using the MUTA-GENE™ phagemid in vitro mutagenesis kit by BIO-RAD. The kit is based on the method described by Kunkel in U.S. Pat. No. 4,873,192. (See also T. Kunkel, *Proc. Natl Acad. Sci. USA* 82:488 (1985); T Kunkel et al., *Methods in Enzymol.* 154:367 (1987)). U.S. Pat. No. 4,873,192 provides a very strong selection against the non-mutagenized strand of a double-stranded DNA. When DNA is synthesized in a dut-ung-double mutant bacterium, the nascent DNA carries a number of uracils in thymine positions as a result of the dut mutation, which inactivates the enzyme dUTPase and results in high intracellular levels of dUTP. The ung mutation inactivates uracil N-glycosylase, which allows the incorporated uracil to remain in the DNA. This uracil-containing strand is then used as the template for the in vitro synthesis of a complementary strand primed by an oligonucleotide containing the desired mutation. When the resulting double-stranded DNA is transformed into a cell with a proficient uracil N-glycosylase, the uracil-containing stand is inactivated with high efficiency, leaving the non-uracil-containing survivor to replicate (see generally BIO-RAD catalog number 170-3576 instruction manual).

The keratinase gene encompassing the DNA encoding keratinase as well as regulatory elements may be constructed by amplification of a selected, or target, nucleic acid sequence. Amplification may be carried out by any suitable means. See generally D. Kwoh and T. Kwoh, *Am. Biotechnol. Lab.* 8:14 (1990). Examples of suitable amplification techniques include, but are not limited to, polymerase chain reaction, ligase chain reaction, strand displacement amplification (see generally G. Walker et al., *Proc. Natl. Acad. Sci. USA* 89:392 (1992); G. Walker et al., *Nucleic Acids Res.* 20:1691 (1992)), transcription-based amplification (see D. Kwoh et al., *Proc. Natl. Acad Sci. USA* 86:1173 (1989)), self-sustained sequence replication (or "3SR") (see J. Guatelli et al., *Proc. Natl. Acad. Sci. USA* 87:1874 (1990)), the Qβ replicase system (see P. Lizardi et al., *Biotechnology* 6:1197 (1988)), nucleic acid sequence-based amplification (or "NASBA") (see R. Lewis, *Genetic Engineering News* 12 9:1 (1992)), the repair chain reaction (or "RCR") (see R. Lewis, supra), and boomerang DNA amplification (or "BDA") (see R. Lewis, supra). Polymerase chain reaction is currently preferred.

DNA amplification techniques such as the foregoing can involve the use of a probe, a pair of probes, or two pairs of probes which specifically bind to DNA encoding the desired target protein.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel.

Ligase chain reaction (LCR) is also carried out in accordance with known techniques. See, e.g., R. Weiss, *Science* 254:1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

A vector is a replicable DNA construct. Vectors are used herein either to amplify DNA encoding a keratinase as given herein and/or to express DNA which encodes a keratinase as given herein. An expression vector is a replicable DNA construct in which a DNA sequence encoding a keratinase is operably linked to suitable control sequences capable of effecting the expression of the keratinase in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a DNA sequence as disclosed herein constructed using recombinant DNA techniques. Transformed host cells ordinarily express the keratinase, but host cells transformed for purposes of cloning or amplifying the keratinase DNA do not need to express the keratinase. Suitable host cells can include host cells known to those skilled in the art, such as for example prokaryote host cells.

Prokaryote host cells include gram negative or gram positive organisms, for example Escherichia coli (E. coli) or Bacilli. Higher eukaryotic cells include established cell lines of mammalian origin as described below. Exemplary host cells are E. coli W3110 (ATCC 27,325), E. coli B, E. coli X1776 (ATCC 31,537), E. coli 294 (ATCC 31,446). A broad variety of suitable prokaryotic and microbial vectors are available. E. coli is typically transformed using pBR322. Promoters most commonly used in recombinant microbial expression vectors include the beta-lactamase (penicillinase) and lactose promoter systems (Chang et al., Nature 275:615 (1978); and Goeddel et al., Nature 281:544 (1979)), a tryptophan (trp) promoter system (Goeddel et al., Nucleic Acids Res. 8:4057 (1980) and EPO App. Publ. No. 36,776) and the tac promoter (H. De Boer et al., Proc. Natl. Acad. Sci. USA 80:21 (1983)). The promoter and Shine-Dalgarno sequence (for prokaryotic host expression) are operably linked to the DNA encoding the keratinase, i.e., they are positioned so as to promote transcription of keratinase messenger RNA from the DNA.

Eukaryotic microbes such as yeast cultures may also be transformed with vectors carrying the isolated DNA's disclosed herein. see, e.g., U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the keratinase as given herein, sequences for polyadenylation and transcription termination, and a selection gene. An exemplary plasmid is YRp7, (Stinchcomb et al., Nature 282:39 (1979); Kingsman et al., Gene 7:141 (1979); Tschemper et al., Gene 10:157 (1980)). Suitable promoting sequences in yeast vectors include the promoters for metallothionein, 3-phosphoglycerate kinase (Hitzeman et al., J. Biol. Chem. 255:2073 (1980) or other glycolytic enzymes (Hess et al., J. Adv. Enzyme Reg. 7:149 (1968); and Holland et al., Biochemistry 17:4900 (1978)). Suitable vectors and promoters for use in yeast expression are further described in R. Hitzeman et al., EPO Publn. No. 73,657.

C. Preparation and Use of Keratinase Enzyme

As noted above, keratinase enzyme can be made by culturing a host cell as described above under conditions that permit expression of the encoded keratinase, and collecting the expressed keratinase. The host cell may be cultured under conditions in which the cell grows, and then cultured under conditions which cause the expression of the encoded keratinase, or the cells may be caused to grow and express the encoded keratinase at the same time. The keratinase may be fused to an appropriate secretory leader sequence or otherwise expressed into the culture media and collected from the media, or the keratinase may be expressed intracellularly, the cells then lysed, and the keratinase collected from the cell lysate. In general, any suitable techniques for culturing and expressing a transgenic protein may be used, as will be appreciated by those skilled in the art.

The prepared keratinase enzyme is useful in processes for degrading keratinaceous material. Exemplary hydrolyzing processes are described in U.S. Pat. Nos. 5,063,161, and 4,959,311 to Shih et al., the disclosures of which are incorporated herein by reference in their entirety. The foregoing patents to Shih et al. also disclose fermentation media which include keratinase enzyme. Accordingly, the keratinase enzyme of the present invention is useful in the preparation of fermentation media.

The prepared keratinase enzyme can also be used to produce a hydrolyzed feather product. Hydrolyzed feather product has several known uses. For example, hydrolyzed feather may be used as an ingredient in animal feed preparations. Similarly, the prepared keratinase enzyme itself may be incorporated into animal feed preparations. U.S. Pat. No. 5,186,961 to Shih et al., the disclosure of which is incorporated herein in its entirety, discloses suitable preparations of animal feed including keratinase enzyme.

The prepared keratinase enzyme is also useful in the production of amino acids from feather products, as discussed above in the Background of the Invention.

The present invention is explained in greater detail in the following non-limiting Example. The example is provided for illustrative purposes only, and is not to be taken as limiting the scope of the invention.

EXAMPLE 1

Isolating and Sequencing the Keratinase Gene from Bacillus licheniformis PWD-1 by PCR-Walking The keratinase enzyme is cleaved using cyanogen bromide according to techniques known to those skilled in the art. Thereafter, the 5' DNA (N10) sequence corresponding to the N-terminal amino acid sequence is used as a fixed primer in conjunction with a series of random primers paired individually to perform the polymerase chain reaction (PCR). Hybridization with a 25-mer oligonucleotide probe downstream of N10 gives a 683 bp PCR product amplified by N10 and one of the random primers, identified as containing part of the keratinase gene. The distal 3' portion of the gene is amplified and sequenced by the same method, using a second fixed primer (I10) designed at position +548 and paired with random primers to perform PCR. Upstream sequence analysis was conducted in a similar manner. An upstream region of 575 bp is amplified by PCR using an antisense 10-mer fixed primer (R10) paired with random primers. The complete 1,457 bp sequence encompassing the *Bacillus licheniformis* keratinase gene and regulatory elements is determined from the combined PCR products.

The identified gene is highly similar to the *Bacillus licheniformis* NCIB 6816 subtilisin Carlsberg gene, as shown in FIG. 1. The variances are identified with the differing Carlsberg gene amino acids in bold above the corresponding amino acid of the identified *Bacillus licheniformis* keratinolytic protease.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1457 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus licheniformis
        ( B ) STRAIN: PWD-1

( i x ) FEATURE:
        ( A ) NAME/KEY: CDS
        ( B ) LOCATION: 215..1354

( x i ) SEQUENCE DESCRIPTION: SEQ ID NO:1:

```
CTCCTGCCAA  GCTGAAGCGG  TCTATTCATA  CTTTCGAACT  GAACATTTTT  CTAAAACAGT      60

TNNTAATAAC  CAAAAAATTT  TAAATTGGCC  CTCCAAAAAA  ATAGGCCTAC  CATATAATTC     120

ATTTTTTTTC  TATAATAAAT  TAACAGAATA  ATTGGAATAG  ATTATATTAT  CCTTCTATTT     180

AAATTATTCT  GAATAAAGAG  GAGGAGAGTG  AGTAATGATG  AGGAAAAAGA  GTTTTTGGCT     240

TGGGATGCTG  ACGGCCTTCA  TGCTCGTGTT  CACGATGGCA  TTCAGCGATT  CCGCTTCTGC     300

TGCTCAACCG  GCGAAAAATG  TTGAAAAGGA  TTATATTGTC  GGATTTAAGT  CAGGAGTGAA     360

AACCGCATCT  GTCAAAAAGG  ACGTCATCAA  AGAGAGCGGC  GGAAAAGTGG  ACAAGCAGTT     420

TAGAATCATC  AACGCAGCAA  AAGCGAAGCT  AGACAAAGAA  GCGCTTAAGG  AAGTCAAAAA     480

TGATCCGGAT  GTCGCTTATG  TGGAAGAGGA  TCATGTGGCC  CATGCCTTGG  CGCAAACCGT     540

TCCTTACGGC  ATTCCTCTCA  TTAAAGCGGA  CAAAGTGCAG  GCTCAAGGCT  TTAAGGGAGC     600

GAATGTAAAA  GTAGCCGTCC  TGGATACAGG  AATCCAAGCT  TCTCATCCGG  ACTTGAACGT     660

AGTCGGCGGA  GCAAGCTTTG  TGGCTGGCGA  AGCTTATAAC  ACCGACGGCA  ACGGACACGG     720

CACACATGTT  GCCGGTACAG  TAGCTGCGCT  TGACAATACA  ACGGGTGTAT  TAGGCGTTGC     780

GCCAAGCGTA  TCCTTGTACG  CGGTTAAAGT  ACTGAATTCA  AGCGGAAGCG  GATCATACAG     840

CGGCATTGTA  AGCGGAATCG  AGTGGGCGAC  AACAAACGGC  ATGGATGTTA  TCAATATGAG     900

CCTTGGGGGA  GCATCAGGCT  CGACAGCGAT  GAAACAGGCA  GTCGACAATG  CATATGCAAG     960

AGGGGTTGTC  GTTGTAGCTG  CAGCAGGGAA  CAGCGGATCT  TCAGGAAACA  CGAATACAAT    1020

TGGCTATCCT  GCGAAATACG  ATTCTGTCAT  CGCTGTTGGT  GCGGTAGACT  CTAACAGCAA    1080

CAGAGCTTCA  TTTTCCAGTG  TGGGAGCAGA  GCTTGAAGTC  ATGGCTCCTG  GCGCAGGCGT    1140

ATACAGCACT  TACCCAACGA  ACACTTATGC  AACATTGAAC  GGAACGTCAA  TGGTTTCTCC    1200
```

```
TCATGTAGCG GGAGCAGCAG CTTTGATCTT GTCAAAACAT CCGAACCTTT CAGCTTCACA      1260

AGTCCGCAAC CGTCTCTCCA GCACGGCGAC TTATTTGGGA AGCTCCTTCT ACTATGGGAA      1320

AGGTCTGATC AATGTCGAAG CTGCCGCTCA ATAACATATT CTAACAAATA GCATATAGAA      1380

AAAGCTAGTG TTTTTAGCAC TAGCTTTTTC TTCATTCTGA TGAAGGTTGT CCAATATTTT      1440

GAATCCGTTC CATGATC                                                    1457
```

( 2 ) INFORMATION FOR SEQ ID NO:2:

( i ) SEQUENCE CHARACTERISTICS:
        ( A ) LENGTH: 379 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Bacillus licheniformis
        ( B ) STRAIN: PWD-1

( x i ) SEQUENCE DESCRIPTION: SEQ ID NO:2:

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Val Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Arg Gly Val Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
```

|  | 275 | | | | | 280 | | | | 285 | | | |
|---|---|---|---|---|---|---|---|---|---|---|---|---|---|
| Asn | Arg<br>290 | Ala | Ser | Phe | Ser | Ser<br>295 | Val | Gly | Ala | Glu | Leu<br>300 | Glu | Val | Met | Ala |
| Pro<br>305 | Gly | Ala | Gly | Val | Tyr<br>310 | Ser | Thr | Tyr | Pro | Thr<br>315 | Asn | Thr | Tyr | Ala | Thr<br>320 |
| Leu | Asn | Gly | Thr | Ser<br>325 | Met | Val | Ser | Pro | His<br>330 | Val | Ala | Gly | Ala | Ala<br>335 | Ala |
| Leu | Ile | Leu | Ser<br>340 | Lys | His | Pro | Asn | Leu<br>345 | Ser | Ala | Ser | Gln | Val<br>350 | Arg | Asn |
| Arg | Leu | Ser<br>355 | Ser | Thr | Ala | Thr | Tyr<br>360 | Leu | Gly | Ser | Ser | Phe<br>365 | Tyr | Tyr | Gly |
| Lys | Gly<br>370 | Leu | Ile | Asn | Val | Glu<br>375 | Ala | Ala | Ala | Gln | | | | | |

That which is claimed is:

1. An isolated DNA molecule encoding a keratinase, said isolated DNA having the DNA sequence of SEQ ID NO: 1.

2. A recombinant DNA molecule comprising vector DNA and an isolated DNA of claim 1 which encodes a keratinase enzyme having the amino acid sequence of SEQ ID NO: 2.

3. A host cell containing a recombinant DNA molecule according to claim 2 which expresses a keratinase enzyme having the amino acid sequence of SEQ ID NO: 2.

4. A method of making a keratinase enzyme, comprising:

culturing a host cell according to claim 3 under conditions which permit expression of the encoded keratinase; and collecting said keratinase enzyme from the host cell culture.

* * * * *